United States Patent [19]

Fehr et al.

[11] 4,296,258

[45] Oct. 20, 1981

[54] PROCESS FOR THE PREPARATION OF MACROCYCLIC KETONES

[75] Inventors: Charles Fehr, Geneva; Günther Ohloff, Bernex, both of Switzerland; Georges H. Büchi, Cambridge, Mass.

[73] Assignee: Firmenich SA, Geneva, Switzerland

[21] Appl. No.: 107,847

[22] Filed: Dec. 28, 1979

[30] Foreign Application Priority Data

Jan. 26, 1979 [CH] Switzerland .......................... 796/79

[51] Int. Cl.$^3$ .............................................. C07C 45/00
[52] U.S. Cl. .................................... 568/364; 568/338; 564/81
[58] Field of Search .............................. 568/338, 364; 260/348.21; 564/81

[56] References Cited

PUBLICATIONS

Ohloff et al., Helv. Chim. Acta, vol. 50 (1967) 705-713.
Industrial Chemicals, 2nd Ed. (1957) 384-388.

Primary Examiner—Bernard Helfin
Attorney, Agent, or Firm—Pennie & Edmonds

[57] ABSTRACT

New process for the preparation of acetylenic macrocyclic ketones, which compounds represent useful intermediates for the synthesis of valuable perfuming ingredients, viz. muscone and EXALTONE ® (cyclopentadecanone).

7 Claims, No Drawings

PROCESS FOR THE PREPARATION OF MACROCYCLIC KETONES

BRIEF SUMMARY OF THE INVENTION

The invention relates to the field of perfumery, in particular it provides a process for the preparation of acetylenic macrocyclic ketones of formula

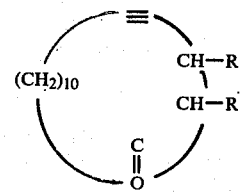

wherein one of symbols R represents a lower alkyl radical containing 1 to 3 carbon atoms and the other a hydrogen atom, which comprises a. treating a hydrazone of formula

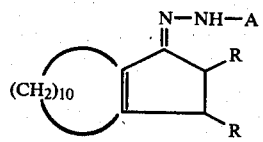

wherein symbols R are defined as above and A designates a sulphonyl radical of formula $$R^1SO_2— \qquad (III)$$

wherein $R^1$ stands for an aryl radical, with a halogenating reagent selected from the group consisting of
  a. bromine,
  b. chlorine,
  c. iodine,
  d. 1,3-dibromo-5,5-dimethyl-hydantoin,
  e. N-bromosuccinimide,
  f. N-iodosuccinimide and
  g. N-chlorosuccinimide in the presence of a lower aliphatic alcohol and at a temperature of from about $-25°$ to about $+25°$ C.;

b. reducing the excess of halogenating reagent, and c. heating the reaction mixture in an aqueous medium at a temperature of from about 20° to about 60° C.

BACKGROUND OF THE INVENTION

Among the most appreciated musky ingredients known in the art of perfumery, muscone (or 3-methyl-cyclopentadecanone) and EXALTONE® (or cyclopentadecanone) have acquired a special renown. In an attempt to develop a large scale preparation of these derivatives, hitherto numerous synthetic approaches have been devised [see e.g. Cosmetics and Perfumery, 88, 67(1973)]. In spite of this undertaking no economical synthetic process has been satisfactorily applied so far to their industrial preparation.

Among the variety of processes known, one may cite the following:

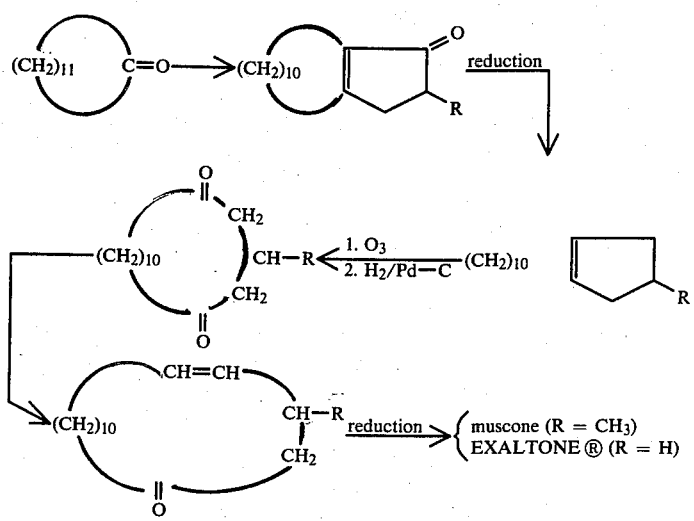

reference: Helv. Chim. Acta, 50, 705 (1967); as well as the following variant

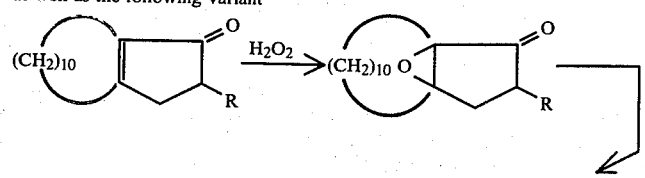

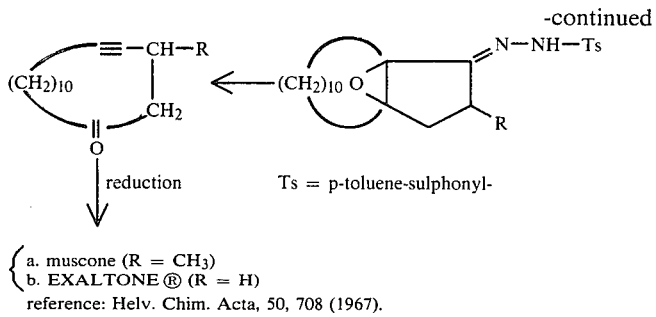

{ a. muscone (R = CH₃)
  b. EXALTONE® (R = H)
reference: Helv. Chim. Acta, 50, 708 (1967).

By making the preparation of certain critical intermediates easier, the novel process of the present invention provides an original solution to the problem of economically synthetizing macrocyclic ketones.

PREFERRED EMBODIMENTS OF THE INVENTION

Hydrazones (II), used as starting materials in the said process, are compounds which could be easily obtained by current methods from their corresponding ketones whose preparation is described namely in U.S. Pat. No. 3,778,482.

In accordance with the invention, compounds (II) represent sulphonyl derivates, namely arylsulphonyls. Thus the sulphonyl group can preferably designate a p-toluene-sulphonyl-, a p-nitro-benzene-sulphonyl or a 2,4-dinitro-benzene-sulphonyl radical.

The reaction which characterizes the process of the invention is effected in the presence of a lower aliphatic alcohol. Suitable alcohols include e.g. methanol, ethanol, n-propanol, iso-propanol, n-butanol or sec-butanol, or a glycol such as ethylene glycol. It has been observed that the best yields of end products were obtained by using iso-propanol or ethylene glycol.

The reaction can be effected by putting the starting hydrazone in suspension either in the chosen alcohol, or in a mixture of said alcohol together with an auxiliary solvent, for instance in admixture with an ether such as tetrahydrofuran, dioxan, or the dimethyl ether of ethylene glycol, acetone or any mixture thereof. As indicated above, the said reaction can be carried out at a temperature of from about −25° to about +25° C., preferably at about −10° C., at which temperature we have observed the best yields in end-products formation. On the other hand, at temperatures higher than the above indicated upper limit, the formation of undesirable by-products tends to diminish somehow the expected overall yield.

The desired acetylenic ketones, when obtained in accordance with the process of the invention, are accompanied by a variable amount of the bicyclic ketones corresponding to the starting hydrazones. The proportions of the desired acetylenic ketones in the said mixtures depend on the nature of the aliphatic alcohol used. Thus, for example, iso-propanol enables the formation of mixtures essentially consisting of the desired acetylenic ketone when the process is applied to the conversion of bicyclo[10.3.0]pentadec-[1(12)]en-13-one p-toluenesulphonyl-hydrazone, whereas higher contents of 3-methylcyclopentadec-1-yn-5-one are obtained by converting 14-methyl-bicyclo[10.3.0]pentadec-[1(12)]-en-13-one in the presence of ethylene glycol.

Reaction times are rather short, of the order of a few minutes, and the course of the reaction is stopped by adding to the reaction mixture a reagent capable to reduce the excess of the halogenating reactant used. To this end, the preferred reagents include alkali metal salts such as sodium or potassium sulphite, bisulphite or thiosulphate in aqueous solution. After the addition of the reducing reagent, the reaction mixture is generally heated to a temperature of from about 20° to about 60° C. The addition itself is exothermic and consequently it can happen that an external heating is superfluous. Finally, the separation of the obtained desired product from the mixture can be effected by applying conventional techniques, for instance by subjecting the mixture to a fractional distillation.

The conversion of the obtained acetylenic ketones of formula (I) into their corresponding saturated derivatives, muscone and EXALTONE® for example, can be carried out in accordance with known methods, e.g. by catalytic hydrogenation [see Chemical Abstracts, 88,169677d].

The invention is better illustrated by but not limited to the following examples wherein the temperatures are indicated in degrees centigrade.

EXAMPLE 1

Cyclopentadec-1-yn-5-one 3.15 g (11 mM) of 1,3-dibromo-5,5-dimethylhydantoin were added at −15° to a vigorously stirred suspension of 3.88 g (10 mM) of bicyclo[10.3.0]pentadec-[1(12)]-en-13-one p-toluene-sulphonyl hydrazone in a 1:1 (volume) mixture of acetone and iso-propanol (80 ml). A strong release of gas was observed while the mixture became red and the temperature increased to −5°. After 3 minutes, the reaction was stopped by the addition of 7.5 ml of a 2.75 M aqueous solution of sodium bisulphite, followed by the addition of 50 ml of water to the resulting yellowish cloudy mixture. After having been left for 30 minutes under stirring at 50°–55° and cooled thereafter, the reaction mixture was treated with 100 ml of petrol ether (b.p. 80°–100°) and 70 g of 50% NaOH aqueous solution. After separation, the aqueous phase was extracted thrice with petrol ether and the combined organic extracts were subjected to the usual treatments of washing with water and with brine then they were dried over sodium sulphate.

The evaporation of the volatile fractions gave 2.59 g of a yellow-red oil consisting of a 9:1 mixture of cyclopentadec-1-yn-5-one and bicyclo[10.3.0]pentadec-[1(12)]-en-13-one.

The desired product was obtained by separating it from the mixture via distillation by means of a bulb apparatus (bath temp. 140°/0.05 Torr). 1.412 g (yield 64%) of the desired product were thus obtained (purity≅90%) The analytical characters of the compound were in all respects identical with those shown by a sample prepared according to a known method [Helv.-Chim.Acta, 54, 2896 (1971)].

EXAMPLE 2

Cyclopentadec-1-yn-5-one

By replacing, in the process described in Example 1 above, 1,3-dibromo-5,5-dimethyl-hydantoin by an equivalent amount (11 mM) of N-bromosuccinimide, almost identical results were obtained.

EXAMPLE 3

3-Methyl-cyclopentadec-1-yn-5-one 20.1 g (50 mM) of 14-methyl-bicyclo[10.3.0]pentadec-[1(12)]-en-13-one p-toluene-sulphonyl hydrazone were dissolved in 500 ml of a 2:2:1 mixture of acetone, tetrahydrofuran and ethylene-glycol, whereupon 20.0 g (112 mM) of N-bromo-succinimide were added to the resulting solution cooled at $-15°$.

A strong gas release occurred during the addition while the mixture became red and the temperature increased to about $-6°$ within 90 seconds.

After 3 minutes, the reaction was stopped by the addition thereto of 50 ml of a 2.75 M solution of sodium bisulphite, followed by 200 ml of water. After having been left 30 minutes at 40°, the mixture was treated as indicated in Example 1 to give 13.8 g of a 5:1 mixture of 3-methyl-cyclopentadec-1-yn-5-one and 14-methyl-bicyclo[10.3.0]pentadec[1(12)]-en-13-one.

6.9 g of this mixture were bulb distilled in the presence of 3 g of potassium carbonate (160°/0.1 Torr) to give 3.16 g (13.5 mM, yield 54%) of a 85/15 mixture of the desired product and 14-methyl-bicyclo[10.3.0]pentadec-[1(12)]-en-13-one. A further purification was effected by means of column chromatography on silica gel (eluant: 19/1 cyclohexane/ethyl acetate) to give pure 3-methyl-cyclopenta-dec-1-yn-5-one, the analytical characters of which were in agreement with those of a sample prepared in accordance with a known method [Helv.Chim.Acta, 54, 2896 (1971)].

EXAMPLE 4

3-Methyl-cyclopentadec-1-yn-5-one

By replacing in above Example 3, N-bromosuccinimide (2.14 equivalents) by an amount equal to 1.1 equivalents of 1,3-dibromo-5,5-dimethyl-hydantoin, analogous results were obtained. The p-toluene-sulphonyl hydrazone derivatives of bicyclo[10.3.0]pentadec-[1(12)]-en-3-one and 14-methyl-bicyclo[10.3.0]pentadec-[1(12)]-en-13-one used as starting materials in the process described in Examples 1 to 4 can be prepared as follows:

Bicyclo[10.3.0 pentadec[1(12)]-en-13-one p-toluene-sulphonyl hydrazone

A suspension of 220 g (1 M) of bicyclo[10.3.0]pentadec-[1(12)]-en-13-one, 205 g (1.1 M) of p-toluene-sulphonyl-hydrazine and 1000 ml of 95% ethanol was heated in a vessel equipped with a lateral distillation apparatus having a Vigreux type column of 20 cm length. The temperature of the mixture was kept at such a value as to enable a slow distillation of the solvent present. While distilling a supplementary amount (1500 ml) of ethanol was added to the mixture. After 7 hours, the reaction mixture was cooled and 100 ml of water were added thereto, then it was kept at 5° for one night while the desired hydrazone crystallized.

The crystalline produce was recovered by filtration and washed with three fractions of 400 ml each of a 4:1 mixture of ethanol and water to give 346.8 g of the desired product having m.p. 150.5°-153°. Another portion of this hydrazone, equivalent to 15.8 g, was separated from the mother liquors by prolonged cooling at about 5°. An analytical sample of the product obtained was purified by cristallization in 95% ethanol:

m.p.: 164°-167°

IR(CDCl$_3$): 3200, 3030-2750, 1615, 1600, 1460, 1440, 1395, 1325, 1180, 1160, 1085, 1015 cm$^{-1}$;

NMR(CDCl$_3$): 7.90 (2H); 7.77 (1H, s); 7.26 (2H); 2.40 (3H, s); 2.5-2.0 (8H, m); 1.9-1.1 (16H, m) δppm;

MS: m/e: 28 (20), 32 (99), 41 (33), 43 (22), 55 (23), 57 (24), 67 (13), 68 (11), 69 (100), 70 (10), 71 (15), 81 (55), 82 (11), 83 (13), 93 (13), 95 (19), 109 (12), 121 (10), 137 (11).

14-Methyl-bicyclo[10.3.0]pentadec-[1(12)]-en-13-one p-toluene-sulphonyl hydrazone This compound was obtained by operating in the same manner as that described hereinabove and by replacing bicyclo[10.3.0]pentadec-[1(12)]-en-13-one by 14-methyl-bicyclo[10.3.0]cyclopentadec[1(12)]-en-13-one. Heating time: 24 h (yield 66.5%).

m.p.(dec.): 134°-140°;

IR(CDCl$_3$): 3230, 3030-2800, 1620, 1600, 1465, 1445, 1395, 1370, 1330, 1160, 1090, 1015 cm$^{-1}$;

NMR(CDCl$_3$): 7.87 (2H); 7.62 (1H); 7.26 (2H); 2.80 (1H); 2.40 (3H, s); 2.6-1.9 (6H, m); 1.9-1.0 (19H, m) δppm;

MS: m/e: 27 (18), 28 (100), 31 (38), 32(37), 39 (20), 41 (26), 43 (27), 44 (93), 45 (17), 48 (12), 55 (22), 64 (27), 65 (13), 67 (10), 77 (11), 79 (15), 81 (12), 91 (78), 92 (50), 93 (18), 94 (34), 105 (16), 106 (12), 107 (21), 119 (14).

EXAMPLE 5

4-Methyl-cyclopentadec-1-yn-5-one

This compound was obtained from 15-methyl-bicyclo[10.3.0]pentadec-[1(12)]-ene-13-one p-toluene sulphonyl hydrazone in accordance with the same procedure as that described in Example 3 above. Yield: 42%; B.p. 150°-170°/0.05 Torr;

IR (CDCl$_3$): 3080-2750, 1705, 1445 and 1365 cm$^{-1}$;

NMR (CDCl$_3$): 2.90-2.10 (7H, m); 1.90-1.00 (19 H, m) δppm;

MS: m/e=27 (26), 28 (54), 29 (30), 31 (22), 39 (18), 41 (54), 43 (34), 44 (27), 45 (100), 55 (35), 57 (17), 59 (23), 67 (18), 77 (15), 79 (28), 80 (17), 81 (29), 93 (14), 95 (30), 108 (40), 109 (58), 121 (90), 122 (19), 123 (15), 135 (27), 149 (14), 163 (17), 177 (10), 191 (10), 234 (98, M+), 235 (18).

The starting p-toluene sulphonyl hydrazone was prepared in accordance with the procedure followed for the preparation of its 14-methyl isomer, as described above. Heating time: 40 h (yield 95%); m.p. (dec.): 173°-175°;

IR: 3200, 3030-2750, 1615, 1600, 1460, 1440, 1390, 1325, 1180, 1160, 1085 and 1015 cm$^{-1}$;

NMR (CDCl$_3$): 7.89 (2H, d); 7.31 (2H, d); 7.26 (1H, s); 2.90-1.90 (10H, m); 2.40 (3H, s); 1.80-0.90 (19H, m) δppm;

MS: 28 (100), 29 (54), 31 (72), 32 (85), 39 (52), 41 (60), 43 (48), 44 (92), 45 (47), 54 (40), 55 (40), 57 (18), 64 (24), 65 (22), 67 (53), 81 (19), 91 (73), 92 (53), 97 (28), 98 (16), 112 (14).

What we claim is:

1. A process for the preparation of acetylenic macrocyclic ketones of formula

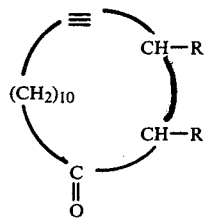  (I)

wherein one of symbols R represents a lower alkyl radical containing 1 to 3 carbon atoms and the other a hydrogen atom, which comprises a. treating a hydrazone of formula

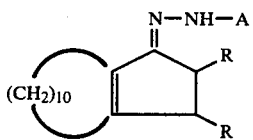  (II)

wherein symbols R are defined as above and A designates a sulphonyl radical of formula

  (III)

wherein R¹ stands for an aryl radical, with a halogenating reagent selected from the group consisting of
a. bromine,
b. chlorine,
c. iodine,
d. 1,3-dibromo-5,5-dimethyl-hydantoin,
e. N-bromosuccinimide,
f. N-iodosuccinimide and
g. N-chlorosuccinimide in the presence of a lower aliphatic alcohol and at a temperature of from about $-25°$ to about $+25°$ C.;

b. reducing the excess of halogenating reagent by addition of reducing agent, and
c. heating the reaction mixture in an aqueous medium at a temperature of from about 20° to about 60° C.

2. Process according to claim 1, wherein the hydrazone of formula (II) is bicyclo[10.3.0]pentadec[1(12)]-en-13-one p-toluene-sulphonyl hydrazone and the obtained acetylenic ketone of formula (I) is cyclopentadec-1-yn-5-one.

3. Process according to claim 1, wherein the hydrazone of formula (II) is 14-methyl-bicyclo[10.3.0]pentadec-[1(12)]-en-13-one p-toluene-sulphonyl hydrazone and the obtained acetylenic ketone of formula (I) is 3-methyl-cyclopentadec-1-yn-5-one.

4. Process according to claim 2, wherein the lower aliphatic alcohol is iso-propanol.

5. Process according to claim 3, wherein the lower aliphatic alcohol is ethylene-glycol.

6. Process according to any of claims 1 to 5, wherein the reduction of the halogenating reagent is effected by means of an alkali metal bisulphite.

7. Process according to any of claims 1 to 5, wherein the treatment of the hydrazone of formula (II) with a halogenating reagent is carried out in the presence of an auxiliary solvent selected from ethers or acetone.

* * * * *